US010165958B2

(12) United States Patent
Matsumura et al.

(10) Patent No.: US 10,165,958 B2
(45) Date of Patent: Jan. 1, 2019

(54) METHOD FOR DETECTING POSITION OF SIGNAL SOURCE IN LIVING BODY, AND DEVICE FOR DETECTING POSITION OF SIGNAL SOURCE IN LIVING BODY

(71) Applicants: TORAY ENGINEERING CO., LTD., Tokyo (JP); THE RITSUMEIKAN TRUST, Kyoto (JP)

(72) Inventors: Junichi Matsumura, Shiga (JP); Chisa Inaka, Shiga (JP); Masaaki Makikawa, Kusatsu (JP); Yusuke Sakaue, Kusatsu (JP)

(73) Assignees: TORAY ENGINEERING CO., LTD., Tokyo (JP); THE RITSUMEIKAN TRUST, Kyoto (JP)

( * ) Notice: Subject to any disclaimer, the term of this patent is extended or adjusted under 35 U.S.C. 154(b) by 78 days.

(21) Appl. No.: 15/524,892

(22) PCT Filed: Nov. 14, 2014

(86) PCT No.: PCT/JP2014/005732
§ 371 (c)(1),
(2) Date: May 5, 2017

(87) PCT Pub. No.: WO2016/075726
PCT Pub. Date: May 19, 2016

(65) Prior Publication Data
US 2017/0354340 A1 Dec. 14, 2017

(51) Int. Cl.
*A61B 5/04* (2006.01)
*A61B 5/0428* (2006.01)
(Continued)

(52) U.S. Cl.
CPC ........ *A61B 5/0428* (2013.01); *A61B 5/04028* (2013.01); *A61B 5/0456* (2013.01); *A61B 5/04085* (2013.01); *A61B 5/04288* (2013.01)

(58) Field of Classification Search
None
See application file for complete search history.

(56) References Cited

U.S. PATENT DOCUMENTS

2002/0045836 A1* 4/2002 Alkawwas ........... A61B 5/0006
600/509

FOREIGN PATENT DOCUMENTS

JP    11-113867 A    4/1999

OTHER PUBLICATIONS

International Search Report for corresponding International Application No. PCT/JP2014/005732, dated Feb. 10, 2015.
(Continued)

*Primary Examiner* — Amanda Hulbert
*Assistant Examiner* — Natasha Patel
(74) *Attorney, Agent, or Firm* — Renner Otto Boisselle & Sklar, LLP

(57) ABSTRACT

A method for detecting a position of a signal source in a living body includes: arranging three electrodes on a surface of the living body and alternately connecting a first external resistance and a second external resistance in parallel between the electrodes and a ground potential; measuring first voltages $V_i$ (i=1, 2, 3) generated at the respective electrodes when the first external resistance is connected in parallel between the electrodes and the ground potential, and second voltages $V_i$ (i=1, 2, 3) generated at the respective electrodes when the second external resistance is connected in parallel between the electrodes and the ground potential; and calculating three ratios $V_i/V'_i$ (i=1, 2, 3) from the first and second voltages $V_i$ and $V'_i$, and detecting the position of the signal source in the living body based on the three ratios $V_i/V'_i$ (i=1, 2, 3).

8 Claims, 7 Drawing Sheets

(51) Int. Cl.
    *A61B 5/0402*     (2006.01)
    *A61B 5/0456*     (2006.01)
    *A61B 5/0408*     (2006.01)

(56)         References Cited

OTHER PUBLICATIONS

Masahiro Yoshiwaki et al., "A New Approach to Estimate ECG Signal Source Using Voltage Divider Technology", Proceedings of the SICE Annual Conference 2014; Sep. 9-12, 2014 Hokkaido University, Sapporo, Japan, pp. 1460-1465.

Yusuke Sakaue et al., "Electroencephalograph with Switching Voltage Divider and its Application to Measurement of Event-Related Potential", Advanced Biomedical Engineering, vol. 3, Jul. 31, 2014, pp. 94-100.

\* cited by examiner

FIG.2
| Step | Electrode | Switching Means SW | S1 | S2 | S3 | Output |
|---|---|---|---|---|---|---|
| 1 | ch1 | A | C | O | O | $V_1$ |
| 2 | ch2 | A | O | C | O | $V_2$ |
| 3 | ch3 | A | O | O | C | $V_3$ |
| 4 | ch1 | B | C | O | O | $V'_1$ |
| 5 | ch2 | B | O | C | O | $V'_2$ |
| 6 | ch3 | B | O | O | C | $V'_3$ |
C: Closed (in conduction)
O: Open (out of conduction)
FIG.3
(a)
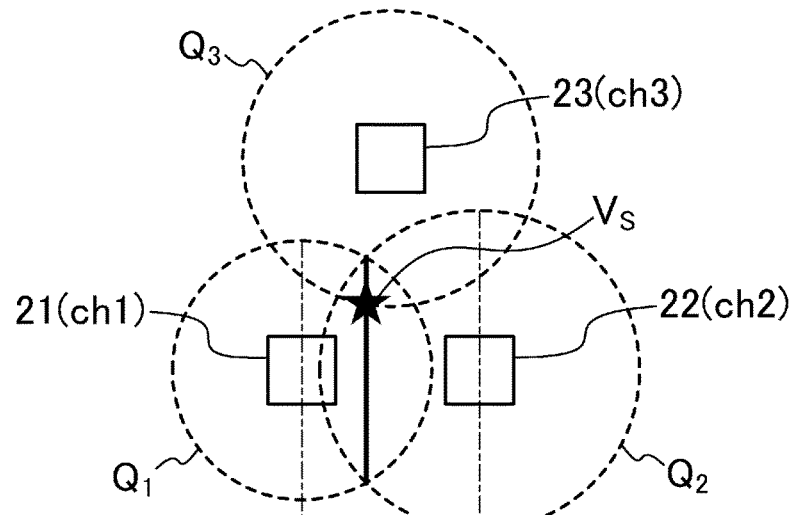
(b)
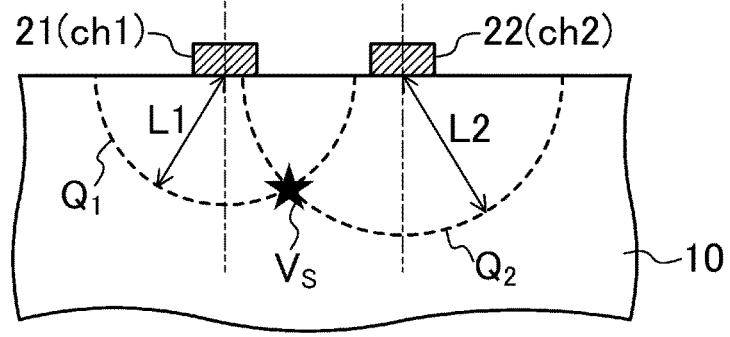

(a)

(b)

FIG.6
| Step | Electrode | Switching Means SW | S1 | S2 | S3 | SS1 | SS2 | SS3 | Output |
|---|---|---|---|---|---|---|---|---|---|
| 1 | ch1 and ch2 | A | C | O | O | O | C | O | $V_{12}$ |
| 2 | ch2 and ch3 | A | O | C | O | O | O | C | $V_{23}$ |
| 3 | ch3 and ch1 | A | O | O | C | C | O | O | $V_{31}$ |
| 4 | ch1 and ch2 | B | C | O | O | O | C | O | $V'_{12}$ |
| 5 | ch2 and ch3 | B | O | C | O | O | O | C | $V'_{23}$ |
| 6 | ch3 and ch1 | B | O | O | C | C | O | O | $V'_{31}$ |
C: Closed (in conduction)
O: Open (out of conduction)
FIG.7
(a)
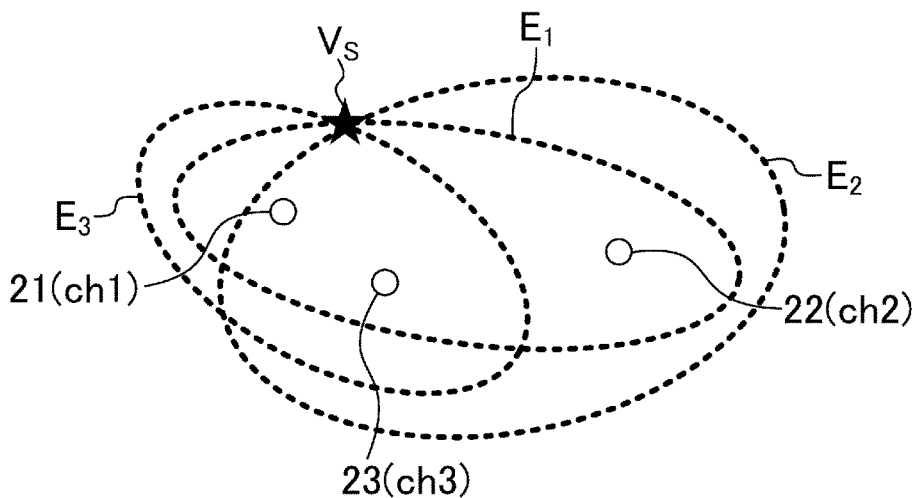
(b)
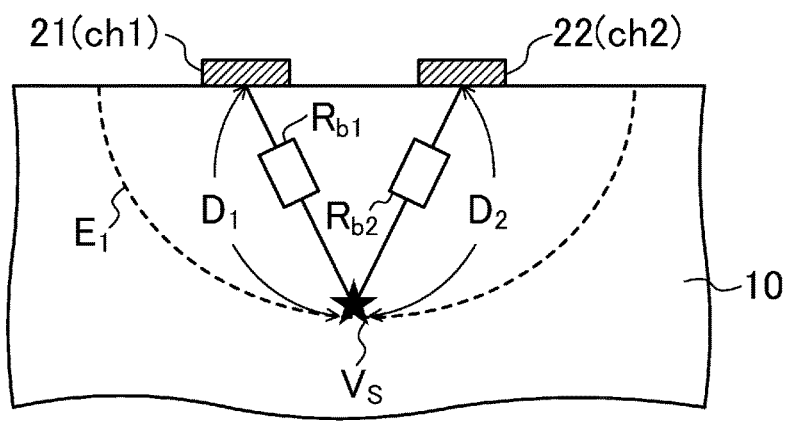

(a)

(b)

(c)

METHOD FOR DETECTING POSITION OF SIGNAL SOURCE IN LIVING BODY, AND DEVICE FOR DETECTING POSITION OF SIGNAL SOURCE IN LIVING BODY

TECHNICAL FIELD

The present invention relates to a method and a device for detecting a position of a signal source in a living body.

BACKGROUND ART

Generally, an electric activity in a living body is measured in the form of an electrocardiogram, for example, by measuring voltages generated at electrodes attached on a surface of the living body.

For example, Patent Document 1 discloses a method including measuring surface potentials at points on a line of intersection (a closed curve) of a living body and a predetermined plane, and determining an electric potential distribution in a cross section, of the living body, passing through the plane.

CITATION LIST

Patent Document

Patent Document 1: Japanese Unexamined Patent Publication No. H11-113867

SUMMARY OF THE INVENTION

Technical Problem

Unfortunately, according the method of Patent Document 1, the measurement need to be performed with a large number of electrodes arranged on a living body without space between the electrodes. Therefore, a considerable burden is imposed on the living body. A decrease in the number of the electrodes will reduce the burden on the living body, but enables acquisition of electric potential distributions in low resolution.

It is therefore an object of the present invention to provide a method and a device which are capable of detecting a position of a signal source in a living body with high accuracy by using a small number of electrodes.

Solution to the Problem

A method according to the present invention detects a position of a signal source in a living body based on voltages generated at a set of electrodes arranged on a surface of a living body. The method includes: arranging the set of electrodes including at least three electrodes on the surface of the living body and alternately connecting a first external resistance and a second external resistance in parallel between the set of electrodes and a ground potential; measuring the voltages including first voltages $V_i$ (i=1, 2, 3) which are generated at the respective electrodes when the first external resistance is connected in parallel between the set of electrodes and the ground potential, and second voltages $V'_i$ (i=1, 2, 3) which are generated at the respective electrodes when the second external resistance is connected in parallel between the set of electrodes and the ground potential; and calculating three ratios $V_i/V'_i$ (i=1, 2, 3) from the first voltages $V_i$ and the second voltages $V'_i$, and detecting the position of the signal source in the living body based on the three ratios $V_i/V'_i$ (i=1, 2, 3).

Another method according to the present invention detects a position of a signal source in a living body based on voltages generated at electrodes arranged on a surface of a living body. The method includes: arranging the electrodes including a first electrode, a second electrode, and a third electrode on the surface of the living body; alternately connecting a first external resistance and a second external resistance in parallel between the first and second electrodes, between the second and third electrodes, and the third and first electrodes; measuring first voltages $V_{12}$, $V_{23}$, and $V_{31}$ which are generated between the respective electrodes when the first external resistance is connected in parallel between the respective electrodes, and second voltages $V'_{12}$, $V'_{23}$, and $V'_{31}$ which are generated between the respective electrodes when the second external resistance is connected in parallel between the respective electrodes; and calculating three ratios $V_{12}/V'_{12}$, $V_{21}/V'_{21}$, and $V_{31}/V'_{31}$ respectively from the first voltages $V_{12}$, $V_{23}$, $V_{31}$ and the second voltages $V'_{12}$, $V'_{23}$, and $V'_{31}$, and detecting the position of the signal source in the living body based on the three ratios $V_{12}/V'_{12}$, $V_{21}/V'_{21}$, and $V_{31}/V'_{31}$.

A device according to the present invention detects a position of a signal source in a living body based on voltages generated at a set of electrodes arranged on a surface of a living body. The device includes: at least three electrodes forming the set of electrodes and being arrangeable on the surface of the living body; a connector alternately connecting a first external resistance and a second external resistance in parallel between the set of electrodes and a ground potential; a measurer measuring, in a state where the set of electrodes has been arranged on the surface of the living body, first voltages $V_i$ (i=1, 2, 3) which are generated at the respective electrodes when the connector connects the first external resistance in parallel between the set of electrodes and the ground potential, and second voltages $V'_i$ (i=1, 2, 3) which are generated at the respective electrodes when the connector connects the second external resistance in parallel between the set of electrodes and the ground potential; and a detector calculating three ratios $V_i/V'_i$ (i=1, 2, 3) from the first voltages $V_i$ and the second voltages $V'_i$, and detecting the position of the signal source in the living body based on the three ratios $V_i/V'_i$ (i=1, 2, 3).

Another device according to the present invention detects a position of a signal source in a living body based on voltages generated at a set of electrodes arranged on a surface of the living body. The device includes: the electrodes including a first electrode, a second electrode, and a third electrode which are arrangeable on the surface of the living body; a connector alternately connecting a first external resistance and a second external resistance in parallel between the first and second electrodes, between the second and third electrodes, and between the third and first electrodes; a measurer measuring, in a state where the electrodes have been arranged on the surface of the living body, first voltages $V_{12}$, $V_{23}$, and $V_{31}$ which are generated between the respective electrodes when the connector connects the first external resistance in parallel between the respective electrodes, and second voltages $V'_{12}$, $V'_{23}$, and $V'_{31}$ which are generated between the respective electrodes when the connectors connects the second external resistance in parallel between the respective electrodes; and a detector calculating three ratios $V_{12}/V'_{12}$, $V_{21}/V'_{21}$, and $V_{31}/V'_{31}$ respectively from the first voltages $V_{12}$, $V_{23}$, $V_{31}$ and the second voltages $V'_{12}$, $V'_{23}$, and $V'_{31}$, and detecting the position of the signal source in the living body based on the three ratios $V_{12}/V'_{12}$, $V_{21}/V'_{21}$, and $V_{31}/V'_{31}$.

Advantages of the Invention

The present invention provides a method and a device which are capable of detecting a position of a signal source in a living body with high accuracy by using a small number of electrodes.

BRIEF DESCRIPTION OF THE DRAWINGS

FIG. 2 is a table showing steps of switching connecting conditions of electrodes and external resistances.

FIG. 3 illustrates, in portions (a) and (b), a method for determining three-dimensional position coordinates of a signal source by using equations of spheres.

FIG. 6 is a table showing steps of switching connecting conditions of electrodes and external resistances.

FIG. 7 illustrates, in portions (a) and (b), a method for determining three-dimensional position coordinates of a signal source by using equations of ellipses.

DESCRIPTION OF EMBODIMENTS

Embodiments of the present invention will be described below in detail with reference to the drawings. Note that the present invention is not limited to the following embodiments. Various changes and modifications may be made without departing from the scope within which the present invention provides advantages. In the following description, the term "electrode" refers to a member attachable to a surface of a living body, the term "potential" refers to an electric level, and the term "voltage" refers to a measured electric level, unless otherwise specified.

First Embodiment

Figure 1:
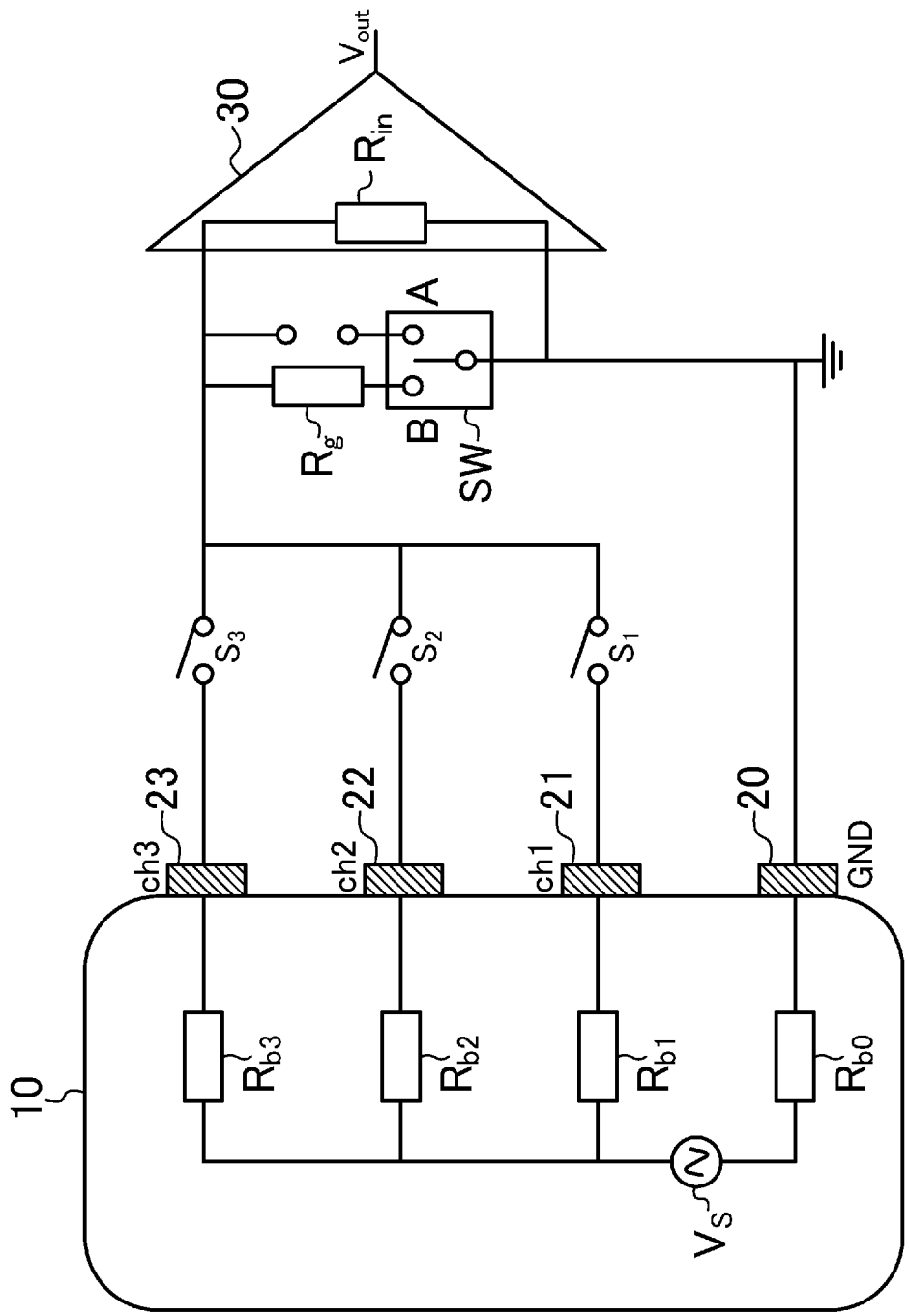
FIG. 1 is a network diagram describing a method for detecting a position of a signal source in a living body, according to a first embodiment of the present invention.

FIG. 1 is a network diagram describing a method for detecting a position of a signal source in a living body, according to a first embodiment of the present invention.

As illustrated in FIG. 1, a set of three electrodes 21, 22, and 23 is arranged on a surface of a living body 10. A first external resistance and a second external resistance which may be switched alternately are connected in parallel between the set of electrodes 21, 22, and 23 and a ground potential. In this embodiment, the first external resistance has an infinite resistance value, and the second external resistor has a resistance value Rg. Thus, the set of electrodes 21, 22, and 23 and the ground potential are connected together by a switching means SW in a switchable manner, via no external resistance or via the external resistance Rg. Note that in this embodiment, although a ground electrode 20 is arranged on the surface of the living body 10 to serve as the ground potential, the ground electrode 20 does not necessarily have to be arranged on the surface of the living body 10.

In this embodiment, the ground electrode 20 is arranged on the surface of the living body 10, and connected to a device for measuring a signal source in a living body, thereby allowing the ground electrode 20 to serve as the ground potential.

A voltage originating from a signal source Vs in the living body 10 is generated at each of the electrodes 21, 22, and 23 arranged on the surface of the living body 10. The voltage is amplified by an amplifier 30, and the amplified voltage is outputted as an output voltage Vout. Switches $S_1$, $S_2$, and $S_3$ are respectively connected between the electrodes 21, 22, and 23 and the amplifier 30. Bringing the switches $S_1$, $S_2$, and $S_3$ into conduction sequentially allows the voltage generated at each of the electrodes 21, 22, and 23 to be measured as the output voltage Vout from the amplifier 30.

In this embodiment, as shown in FIG. 2, the switching means SW and the switches $S_1$, $S_2$, and $S_3$ are switched respectively (Steps 1-6). In this manner, measurements are made of first voltages $V_1$, $V_2$, and $V_3$ which are generated respectively at the electrodes 21, 22, and 23 when no external resistance is connected between the set of electrodes 21, 22, and 23 and the ground potential, and second voltages $V'_1$, $V'_2$, and $V'_3$ which are generated respectively at the electrodes 21, 22, and 23 when the external resistance Rg is connected between the set of electrodes 21, 22, and 23 and the ground potential. In FIG. 2, the electrodes 21, 22, and 23 are indicated as channels $ch_1$, $ch_2$, and $ch_3$, respectively.

Here, in Step 1, the first voltage $V_1$ generated (when no external resistance is connected) at the electrode 21 ($ch_1$) is given by eq. (1).

[Eq. 1]

$$V_{out} = V_1 = V_s \quad \text{(Eq. 1)}$$

On the other hand, in Step 4, the second voltage $V'_1$ generated (when the external resistance Rg is connected) at the electrode 21 ($ch_1$) is given by eq. (2) if input resistance $R_{in}$ of the amplifier 30 is very large. Here, $R_{b1}$ represents a value of internal resistance between the signal source Vs in the living body 10 and the electrode 21 ($ch_1$), and $R_{b0}$ represents a value of internal resistance between the signal source Vs and the ground electrode 20.

[Eq. 2]

$$V_{out} = V'_1 = \frac{R_g}{R_{b1} + R_{b0} + R_g} V_s \quad \text{(Eq. 2)}$$

From the eqs. (1) and (2), a ratio (attenuation ratio) $V'_1/V_1$ between the first voltage $V_1$ generated at the electrode 21 ($ch_1$) when no external resistance is connected and the second voltage $V'_1$ generated at the electrode 21 ($ch_1$) when the external resistance Rg is connected is given by eq. (3).

[Eq. 3]

$$\frac{V'_1}{V_1} = \frac{R_g}{R_{b1} + R_{b0} + R_g} \quad \text{(Eq. 3)}$$

Likewise, a ratio (attenuation ratio) $V'_2/V_2$ between the first voltage $V_2$ generated at the electrode 22 ($ch_2$) when no external resistance is connected and the second voltage $V'_2$ generated at the electrode 22 ($ch_2$) when the external resistance Rg is connected is given by eq. (4). A ratio (attenuation ratio) $V'_3/V_3$ between the first voltage $V_3$ generated at the electrode 23 ($ch_3$) when no external resistance is connected and the second voltage $V'_3$ generated at the electrode 23 ($ch_3$) when the external resistance Rg is connected is given by eq. (5).

[Eq. 4]

$$\frac{V'_2}{V_2} = \frac{R_g}{R_{b2} + R_{b0} + R_g} \quad \text{(Eq. 4)}$$

[Eq. 5]

$$\frac{V'_3}{V_3} = \frac{R_g}{R_{b3} + R_{b0} + R_g} \quad \text{(Eq. 5)}$$

Here, $R_{b2}$ represents a value of internal resistance between the signal source Vs in the living body 10 and the electrode 22 ($ch_2$), and $R_{b3}$ represents a value of internal resistance between the signal source Vs in the living body 10 and the electrode 23 ($ch_3$).

In the meanwhile, if the assumption is made that conductivity inside the living body 10 is uniform, each of the internal resistance values $R_{b1}$, $R_{b2}$, and $R_{b3}$ is considered to be proportional to a respective one of distances from the signal source Vs in the living body 10 to the electrodes 21, 22, and 23. Thus, from the eqs. (3), (4), and (5), the distances $L_1$, $L_2$, and $L_3$ from the signal source Vs in the living body 10 to the electrodes 21, 22, 23 are given by eqs. (6), (7), and (8), respectively.

[Eq. 6]

$$L_1 = \beta R_{b1} = \beta\left\{\left(\frac{V_1}{V'_1} - 1\right)R_g - R_{b0}\right\} \quad \text{(Eq. 6)}$$

[Eq. 7]

$$L_2 = \beta R_{b2} = \beta\left\{\left(\frac{V_2}{V'_2} - 1\right)R_g - R_{b0}\right\} \quad \text{(Eq. 7)}$$

[Eq. 8]

$$L_3 = \beta R_{b3} = \beta\left\{\left(\frac{V_3}{V'_3} - 1\right)R_g - R_{b0}\right\} \quad \text{(Eq. 8)}$$

Here, $\beta$ is a constant defined, for example, by the conductivity of the living body 10.

The eqs. (6), (7), and (8) indicate that each of the distances $L_1$, $L_2$, and $L_3$ is expressed as a function of the reciprocal of a respective one of the attenuation ratios ($V'_1/V_1$, $V'_2/V_2$, and $V'_3/V_3$). As illustrated in the portions (a) and (b) of FIG. 3, the signal source Vs is considered to exist at a point of intersection of three spheres $Q_1$, $Q_2$, and $Q_3$ each of which has a center on a respective one of the electrodes 21, 22, and 23, and a radius corresponding to a respective one of $L_1$, $L_2$, and $L_3$. Thus, three-dimensional position coordinates (x, y, z) of the signal source Vs may be determined by solving the eqs. (9), (10), and (11) of the three spheres $Q_1$, $Q_2$, and $Q_3$. Here, the position coordinates of the electrodes 21, 22, and 23 are denoted by ($a_1$, $b_1$, $c_1$), ($a_2$, $b_2$, $c_2$), and ($a_3$, $b_3$, $c_3$), respectively.

[Eq. 9]

$$(x-a_1)^2 + (y-b_1)^2 + (z-c_1)^2 = L_1^2 \quad \text{(Eq. 9)}$$

[Eq. 10]

$$(x-a_2)^2 + (y-b_2)^2 + (z-c_2)^2 = L_2^2 \quad \text{(Eq. 10)}$$

[Eq. 11]

$$(x-a_3)^2 + (y-b_3)^2 + (z-c_3)^2 = L_3^2 \quad \text{(Eq. 11)}$$

For solving the eqs. (9), (10), and (11), the constant $\beta$ and $R_{b0}$ may be estimated and determined based on, for example, a radioscopic image of the living body 10, containing the signal source Vs.

According to this embodiment, the external resistances are connected in parallel between the set of three electrodes 21, 22, and 23 that are arranged on the surface of the living body 10 and the ground potential, and the connecting conditions are switched to measure the ratio (attenuation ratio) of the voltages generated at each of the electrodes 21, 22, and 23, thereby easily detecting the three-dimensional position of the signal source Vs in the living body 10. Thus, this embodiment of the present invention enables accurate detection of the three-dimensional position of the signal source Vs in the living body, using a small number of electrodes.

Note that although this embodiment has been described on the assumption that the living body 10 has one signal source Vs therein, two or more signal sources may actually be generated at the same time. Even in such a case, according to this embodiment, among the multiple signal sources, one signal source of the most predominant electric signal may be determined as the target signal source.

In this embodiment, depending on the estimated values of the constant $\beta$ and $R_{b0}$, it is not always possible to determine the position of one point of intersection from the three equations, i.e., the eqs. (9), (10), and (11). However, even in such a case, an area in which the point of intersection is positioned may be narrowed down to a certain degree from the eqs. (9), (10), and (11). For example, a center of the thus narrowed area may be detected as the position of the signal source Vs.

In this embodiment, the conductivity inside the living body 10 is assumed to be uniform. Nevertheless, due to interposition of different tissues such as bones and fat, the conductivity inside the living body 10 is not always uniform actually. Even in such a case, however, influence of a change in the conductivity inside the living body 10 may be reduced by contriving ways such as arranging the electrodes 21, 22, and 22 at positions where the interposition of different tissues is absent, thereby enabling accurate detection of the position of the signal source Vs.

In this embodiment, as illustrated in FIG. 2, the switching means SW and the switches $S_1$, $S_2$, and $S_3$ are switched to sequentially measure the first voltages $V_1$, $V_2$, and $V_3$ and the second voltages $V'_1$, $V'_2$, and $V'_3$ at the electrode 21, 22, and 23. Therefore, if the potential of the signal source Vs varies during the switching of these components, the measurement of the position of signal source Vs may contain an error. It is therefore beneficial to perform the switching of the electrodes and the external resistances as quickly as possible. For example, the switching is performed within 1 µs or less, and suitably within 0.1 µs or less.

In this embodiment, the first external resistance has an infinite resistance value (out of conduction) and the second external resistance has a resistance value Rg. However, the first external resistance may have a different resistance value from that of the second external resistance.

If the first external resistance has such a resistance value, in the method for detecting a signal source in a living body according to this embodiment, a set of three electrodes 21, 22, and 23 is arranged on a surface of a living body 10, and a first external resistance and a second external resistance which can be alternately switched are connected in parallel between the set of electrodes 21, 22, and 23 and a ground potential. Then, measurement are made of first voltages $V_i$ (i=1, 2, 3) which are generated respectively at the electrodes 21, 22, and 23 when the first external resistance is connected in parallel between the set of electrodes 21, 22, and 23 and the ground potential, and second voltages $V'_i$ (i=1, 2, 3) which are generated respectively at the electrodes 21, 22, and 23 when the second external resistance is connected in parallel between the set of electrodes 21, 22, and 23 and the ground potential. Three ratios $V_i/V'_i$ (i=1, 2, 3) are then calculated from the first voltages $V_i$ and the second voltages $V'_i$, and the position of the signal source Vs in the living body may be suitably detected based on the three ratios $V_i/V'_i$ (i=1, 2, 3).

As can be seen, the method for detecting a position of a signal source in a living body according to this embodiment includes calculating the ratios $V_i/V'_i$ (i=1, 2, 3) between the first voltages $V_i$ (i=1, 2, 3) and the second voltages $V'_i$ (i=1, 2, 3) that are generated at the respective electrodes 21, 22, and 23 in Steps 1-6, and detecting the three-dimensional position of the signal source Vs in the living body based on the calculated three ratios $V_i/V'_i$ (i=1, 2, 3). Therefore, repeating, as one cycle, the measurements of the ratios $V_i/V'_i$ (i=1, 2, 3) in Steps 1-6 enables acquisition of time-series measurement data of the voltage ratios, and a trajectory of movement of the three-dimensional position of the signal source Vs in the living body may be detected in real time based on the time-series measurement data.

Figure 4:
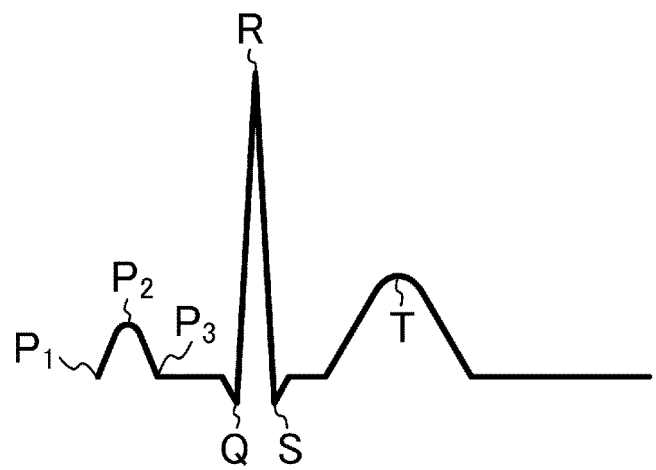
FIG. 4 conceptually illustrates, in portions (a) and (b), a result of measurement of an electric potential of a heart, conducted using a method for detecting a position of a signal source in a living body according to the present invention.
Figure 4:
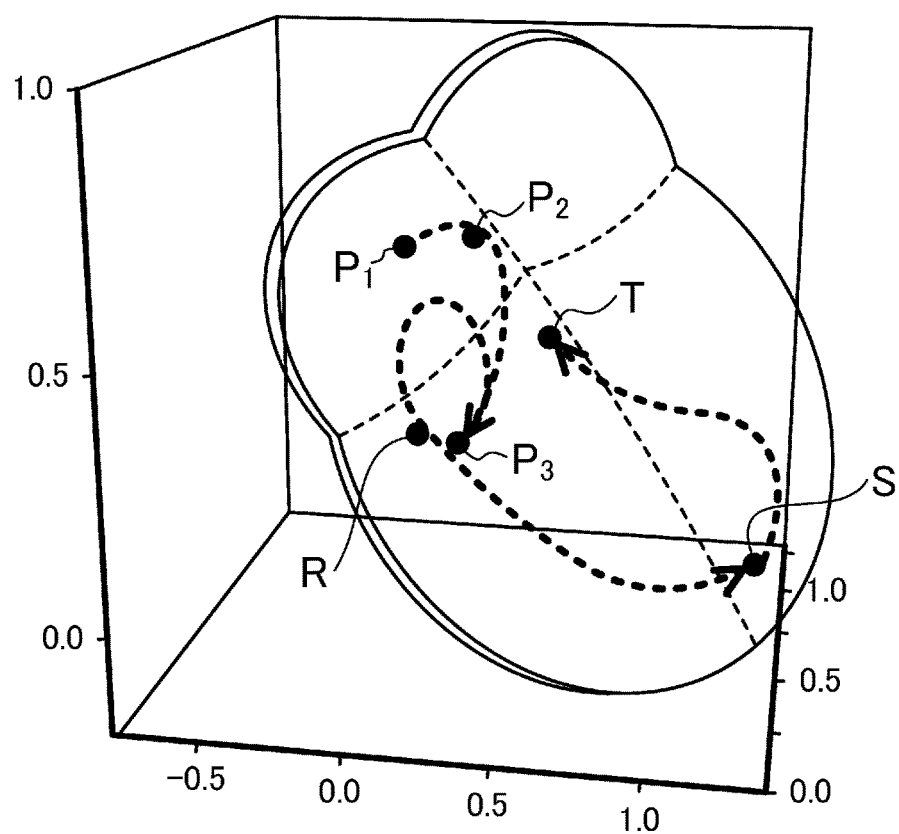

FIG. 4 conceptually illustrates, in the portions (a) and (b), a result of measurement of an electric potential of a heart by using the method for detecting a position of a signal source in a living body according to this embodiment. The portion (a) of FIG. 4 illustrates voltage waveforms (i.e., an electrocardiogram) of a signal source measured by the electrodes. In the portion (b) of FIG. 4, the broken line indicates a trajectory of movement of the three-dimensional position of the signal source which is calculated based on the voltage ratios $V_i/V'_i$ (i=1, 2, 3) of the electrodes. Points $P_1$, $P_2$, $P_3$, R, S, and T on the trajectory of movement indicated by the broken line in the portion (b) of FIG. 4 respectively represent the three-dimensional positions of the signal source corresponding to points $P_1$, $P_2$, $P_3$, R, S, and T on the voltage waveforms illustrated in the portion (b) of FIG. 4. As illustrated in the portion (b) of FIG. 4, it may be detected, in real time, that the signal source of electric activity of the heart moves from an atrium to a ventricle.

If an abnormal waveform such as arrhythmia is observed in the voltage waveforms (electrocardiogram), the signal source from which the abnormal waveform originates may be located in the heart. Thus, the method according to this embodiment of the present invention is effective at diagnosing diseases such as arrhythmia.

FIG. 1 also illustrates a configuration of a device for detecting a position of a signal source in a living body, according to this embodiment of the present invention.

As illustrated in FIG. 1, the device for detecting a position of a signal source in a living body according to this embodiment includes a set of at least three electrodes 21, 22, and 23 arranged on a surface of a living body 10, and a switching means SW switching to alternately connect a first external resistance and a second external resistance in parallel between the set of electrodes 21, 22, and 23 and a ground potential. The device further includes an amplifier (a measurer) 30 and a group of switches $S_1$, $S_2$, and $S_3$. The amplifier 30 measures, in a state where the electrodes 21, 22, and 23 have been arranged on the surface of the living body 10, first voltages $V_i$ (i=1, 2, 3) which are generated respectively at the electrodes 21, 22, and 23 when the switching means SW switches to connect the first external resistance in parallel between the set of electrodes 21, 22, and 23 and the ground potential, and second voltages $V'_i$ (i=1, 2, 3) which are generated respectively at the electrodes 21, 22, and 23 when the switching means SW switches to connect the second external resistance in parallel between the set of electrodes 21, 22, and 23 and the ground potential. The device also includes a detector (not shown) which calculates three ratios $V_i/V'_i$ (i=1, 2, 3) from the first voltages $V_i$ and the second voltages $V'_i$, and detects the position of a signal source in the living body based on the three ratios $V_i/V'_i$ (i=1, 2, 3). Note that the detector may be configured as, for example, a CPU which computes the measurement data provided by the amplifier 30.

Second Embodiment

Figure 5:
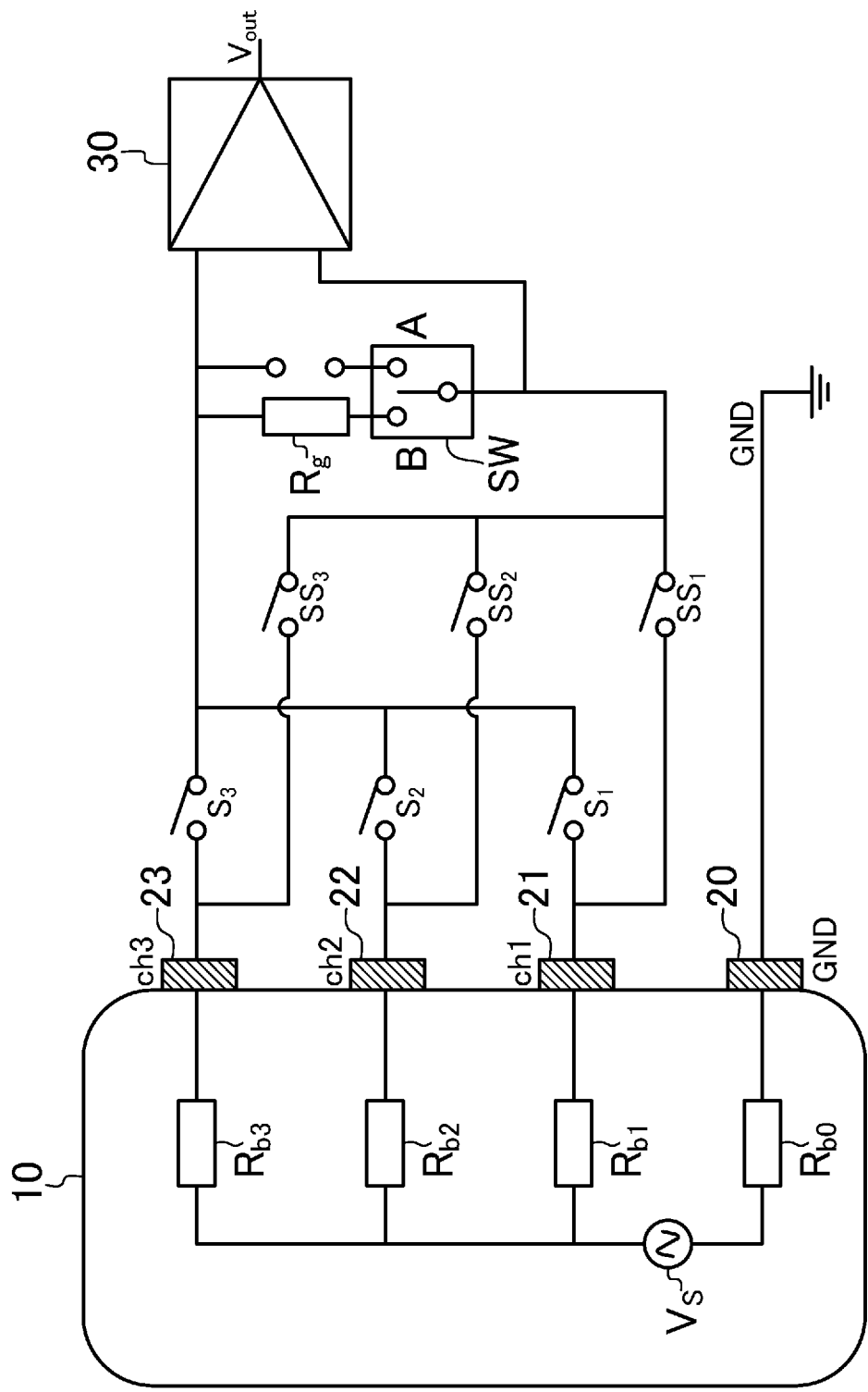
FIG. 5 is a network diagram describing a method for detecting a position of a signal source in a living body, according to a second embodiment of the present invention.

FIG. 5 is a network diagram describing a method for detecting a position of a signal source in a living body, according to a second embodiment of the present invention.

As illustrated in FIG. 5, three electrodes 21, 22, and 23 are arranged on a surface of a living body 10. A first external resistance and a second external resistance which may be switched alternately are connected in parallel between the first electrode 21 and the second electrode 22, between the second electrode 22 and the third electrode 23, and between the third electrode 23 and the first electrode 21. Like the first embodiment, the first external resistance has an infinite resistance value, and the second external resistance has a resistance value Rg. Further, in this embodiment, a ground electrode 20 is arranged on the surface of the living body 10 and serves as a ground potential.

As illustrated in FIG. 5, switches $S_1$, $S_2$, and $S_3$ and switches $SS_1$, $SS_2$, and $SS_3$ are respectively connected between the electrodes 21, 22, and 23 and a differential amplifier 30. Bringing the switches $S_1$, $S_2$, and $S_3$ and the switches $SS_1$, $SS_2$, and $SS_3$ into conduction sequentially as shown in FIG. 6 allows each of voltages generated between the first and second electrodes 21 and 22, the second and third electrodes 22 and 23, and the third and first electrodes 23 and 21 to be measured as an output voltage Vout from the differential amplifier 30. Two of the electrodes are connected to each other by a switching means SW in a switchable manner, via no external resistance or via the external resistance Rg. Thus, as shown in FIG. 6, the switching means SW and the switches $S_1$, $S_2$, $S_3$, $SS_1$, $SS_2$, and $SS_3$ are switched respectively (Steps 1-6). In this manner, measurement are made of first voltages $V_{12}$, $V_{23}$, and $V_{31}$ which are generated between the respective electrodes when no external resistance is connected between the electrodes, and second voltages $V'_{12}$, $V'_{23}$, and $V'_{31}$ which are generated between the respective electrodes when the external resistance Rg is connected between the electrodes. For example, when no external resistance is connected, the first voltage $V_{12}$ generated between the electrodes 21 and 22 may be measured by bringing the switches $S_1$ and $SS_2$ into conduction and switching the switching means SW to the side A. Note that in FIG. 5, the electrodes 21, 22, and 23 are indicated as channels $ch_1$, $ch_2$, and $ch_3$, respectively.

In this embodiment, a ratio (attenuation ratio) $V'_{12}/V_{12}$ between the first voltage $V_{12}$ and the second voltage $V'_{12}$ that are generated between the electrodes 21 and 22 (i.e., between the channels $ch_1$ and $ch_2$) is given by eq. (12).

[Eq. 12]

$$\frac{V'_{12}}{V_{12}} = \frac{R_g}{R_{b1} + R_{b2} + R_g} \quad \text{(Eq. 12)}$$

Here, $R_{b1}$ represents a value of internal resistance between the signal source Vs in the living body 10 and the electrode 21 ($ch_1$), and $R_{b2}$ represents a value of internal resistance between the signal source Vs and the electrode 22 ($ch_2$).

Likewise, a ratio (attenuation ratio) $V'_{23}/V_{23}$ between the first voltage $V_{23}$ and the second voltage $V'_{23}$ that are generated between the electrodes 22 and 23 (between the channels $ch_2$ and $ch_3$) is given by eq. (13). A ratio (attenuation ratio) $V'_{31}/V_{31}$ between the first voltage $V_{31}$ and the second voltage $V'_{31}$ that are generated between the electrodes 23 and 21 (between the channels $ch_3$ and $ch_1$) is given by eq. (14).

[Eq. 13]

$$\frac{V'_{23}}{V_{23}} = \frac{R_g}{R_{b2} + R_{b3} + R_g} \quad \text{(Eq. 13)}$$

[Eq. 14]

$$\frac{V'_{31}}{V_{31}} = \frac{R_g}{R_{b3} + R_{b1} + R_g} \quad \text{(Eq. 14)}$$

Here, $R_{b3}$ represents a value of internal resistance between the signal source Vs in the living body 10 and the electrode 23 ($ch_3$).

It should be noted that unlike the eqs. (3), (4), and (5), the eqs. (12), (13), and (14) do not contain the internal resistance $R_{b0}$ between the signal source Vs and the ground electrode 20.

In the measurement of the voltages generated between two of the electrodes, the internal resistance in the living body 10 is expressed as the sum of the values of internal resistance between each of the two electrodes and the signal source. For example, in the measurement of the first voltage $V_{12}$ and the second voltage $V'_{12}$ that are generated between the electrodes 21 and 22 (between the channels $ch_1$ and $ch_2$), the internal resistance in the living body 10 is expressed as $R_{b1}+R_{b2}$.

Here, if the assumption is made that conductivity inside the living body 10 is uniform, the sum of the values of internal resistance ($R_{b1}+R_{b2}$) is considered to be proportional to the sum ($D_1+D_2$) of a distance $D_1$ from the electrode 21 to the signal source Vs and a distance $D_2$ from the electrode 22 to the signal source Vs, as illustrated in the portion (b) of FIG. 7. Accordingly, from the eq. (12), (13), and (14), the sums of distances ($D_1+D_2$), ($D_2+D_3$), ($D_3+D_1$) between each electrode and the signal source Vs are given by eqs. (15), (16), and (17), respectively.

[Eq. 15]

$$D_1 + D_2 = \alpha(R_{b1} + R_{b2}) = \alpha\left(\frac{V_{12}}{V'_{12}} - 1\right)R_g \quad \text{(Eq. 15)}$$

[Eq. 16]

$$D_2 + D_3 = \alpha(R_{b2} + R_{b3}) = \alpha\left(\frac{V_{23}}{V'_{23}} - 1\right)R_g \quad \text{(Eq. 16)}$$

[Eq. 17]

$$D_3 + D_1 = \alpha(R_{b3} + R_{b1}) = \alpha\left(\frac{V_{31}}{V'_{31}} - 1\right)R_g \quad \text{(Eq. 17)}$$

Here, $\alpha$ represents a constant defined, for example, by the conductivity of the living body 10.

The eqs. (15), (16), and (17) indicate that each of the sums of distances ($D_1+D_2$), ($D_2+D_3$), ($D_3+D_1$) between each electrode and the signal source Vs is expressed as a function of the reciprocal of a respective one of the attenuation ratios ($V'_{12}/V_{12}$), ($V'_{23}/V_{23}$), and ($V'_{31}/V_{31}$). As illustrated in the portions (a) and (b) of FIG. 7, the signal source Vs is considered to exist at a point of intersection of an ellipse $E_1$ having focal points at the electrodes 21 and 22 (the channels $ch_1$ and $ch_2$), an ellipse $E_2$ having focal points at the electrodes 22 and 23 (the channels $ch_2$ and $ch_3$), and an ellipse $E_3$ having focal points at the electrodes 23 and 21 (the channels $ch_3$ and $ch_1$). Thus, the three-dimensional position coordinates (x, y, z) of the signal source Vs may be determined by solving eqs. (18), (19), and (20) of the ellipses $E_1$, $E_2$, and $E_3$. Here, the position coordinates of the electrodes 21, 22, and 23 are denoted by ($a_1$, $b_1$, $c_1$), ($a_2$, $b_2$, $c_2$), ($a_3$, $b_3$, $c_3$), respectively.

[Eq. 18]

$$\sqrt{(x-a_1)^2+(y-b_1)^2+(z-c_1)^2} + \sqrt{(x-a_2)^2+(y-b_2)^2+(z-c_2)^2} = D_1+D_2 \quad \text{(Eq. 18)}$$

[Eq. 19]

$$\sqrt{(x-a_2)^2+(y-b_2)^2+(z-c_2)^2} + \sqrt{(x-a_3)^2+(y-b_3)^2+(z-c_3)^2} = D_2+D_3 \quad \text{(Eq. 19)}$$

[Eq. 20]

$$\sqrt{(x-a_3)^2+(y-b_3)^2+(z-c_3)^2} + \sqrt{(x-a_1)^2+(y-b_1)^2+(z-c_1)^2} = D_3+D_1 \quad \text{(Eq. 20)}$$

For solving the eqs. (18), (19), and (20), the constant $\alpha$ may be estimated and determined, in advance, based on a radioscopic image of the living body 10, showing the signal source Vs.

Unlike the (9), (10), and (11) described in the first embodiment, the eqs. (18), (19), and (20) of this embodiment do not contain the value $R_{b0}$ of internal resistance between the signal source Vs and the ground electrode 20. Thus, the three-dimensional position of the signal source Vs may be detected more accurately.

FIG. 5 also illustrates a configuration of a device for detecting a position of a signal source in a living body, according to this embodiment of the present invention.

As illustrated in FIG. 5, the device for detecting a position of a signal source in a living body according to this embodiment includes at least three electrodes 21, 22, and 23 arranged on a surface of a living body 10, and a switching means SW switching to alternately connect a first external resistance and a second external resistance in parallel between the electrodes 21, 22, and 23. The device further includes a differential amplifier (a measurer) 30 and a group of switches $S_1$, $S_2$, $S_3$, $SS_1$, $SS_2$, and $SS_3$. The differential amplifier 30 measures, in a state where the electrodes 21, 22, and 23 have been arranged on the surface of the living body 10, first voltages $V_i$ (i=1, 2, 3) which are generated respectively at the electrodes 21, 22, and 23 when the switching means SW switches to connect the first external resistance in parallel between the electrodes 21, 22, and 23, and second voltages $V'_i$ (i=1, 2, 3) which are generated respectively at the electrodes 21, 22, and 23 when the switching means SW switches to connect the second external resistance in parallel between the electrodes 21, 22, and 23. The device also includes a detector (not shown) which calculates three ratios $V_i/V'_i$ (i=1, 2, 3) from the first voltages $V_i$ and the second voltages $V'_i$, and detects the position of a signal source Vs in the living body based on the three ratios $V_i/V'_i$ (i=1, 2, 3). Note that the detector may be configured as, for example, a CPU which computes measurement data from the differential amplifier 30.

Third Embodiment

Figure 8:
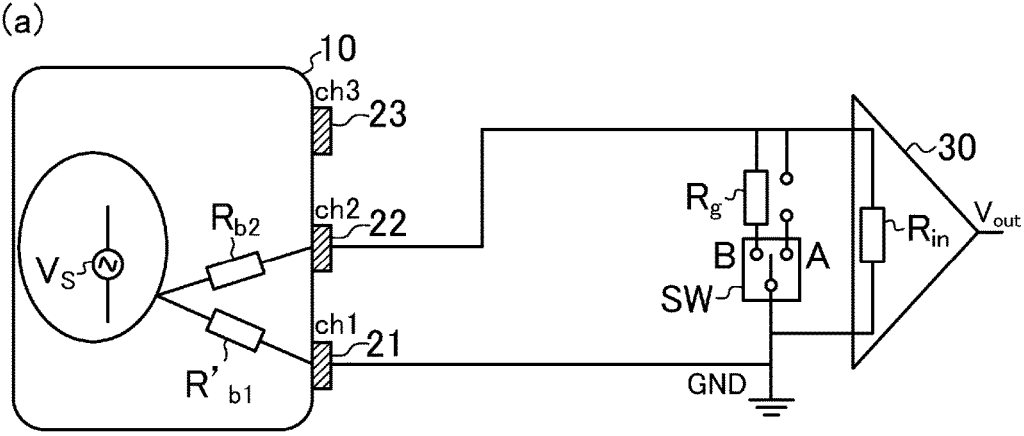
FIG. 8 is a network diagram describing a method for detecting a position of a signal source in a living body, according to a third embodiment of the present invention.
Figure 8:
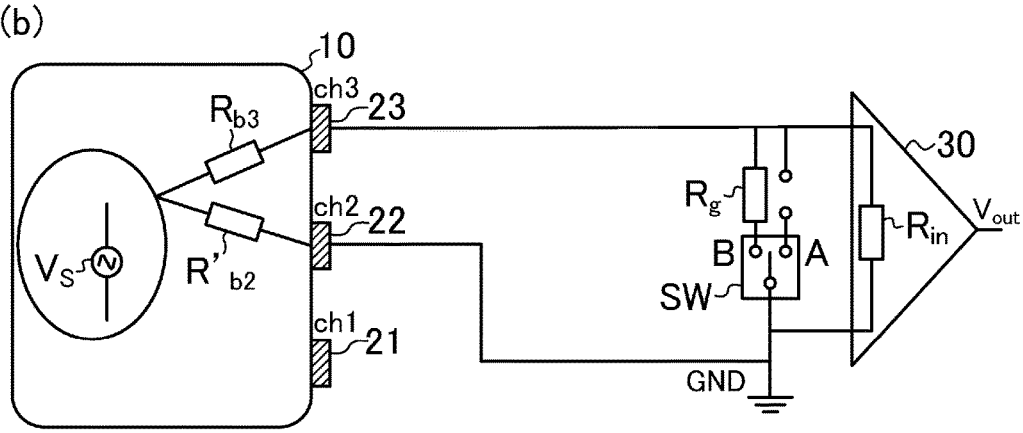
Figure 8:
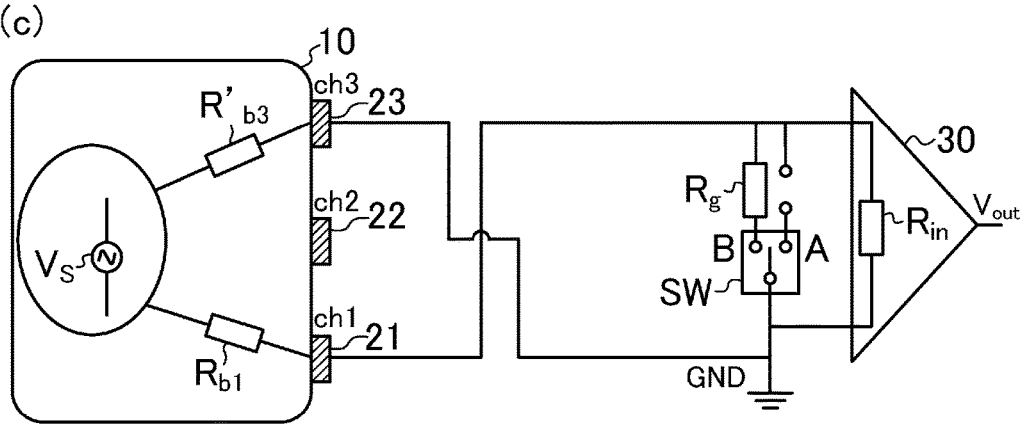

The portions (a)-(c) of FIG. 8 are a network diagram describing a method for detecting a position of a signal source in a living body, according to a third embodiment of the present invention.

The method for detecting a position of a signal source in a living body according to this embodiment is an embodiment of the first embodiment. In the method of this embodiment, when measurements are made of one of first voltages $V_i$ (i=1, 2, 3) and one of second voltages $V'_i$ (i=1, 2, 3) which are generated at a respective one of electrodes 21, 22, and 23, at least one of the other two electrodes is connected to a ground potential.

For example, as illustrated in the portion (a) of FIG. 8, when measurements are made of the first voltage $V_2$ and the second voltage $V'_2$ that are generated at the electrode 22 (the channel $ch_2$), the electrode 21 (the channel $ch_1$) is connected to the ground potential. As illustrated in the portion (b) of FIG. 8, when measurements are made of the first voltage $V_3$ and the second voltage $V'_3$ that are generated at the electrode 23 (the channel $ch_3$), the electrode 22 (the channel $ch_2$) is connected to the ground potential. As illustrated in the portion (c) of FIG. 8, when measurements are made of the first voltage $V_1$ and the second voltage $V'_1$ that are generated at the electrode 21 (the channel $ch_1$), the electrode 23 (the channel $ch_3$) is connected to the ground potential.

Note that in the portions (a)-(c) of FIG. 8, internal resistances between the electrodes 21, 22, and 23 connected to the ground potential and the signal source Vs are indicated respectively as $R'_{b1}$, $R'_{b2}$, and $R'_{b3}$, for the following reasons.

In the present invention, the living body is regarded as a network comprised of a signal source and a large number of resistances. The resistance values between the signal source Vs and the electrodes 21, 22, and 23 and between the signal source Vs and the ground electrode are obtained as values of combined resistance of a network between the signal source Vs and the electrodes and values of combined resistance of a network between the signal source Vs and the ground electrode. Therefore, a different combination of an electrode connected to the ground potential and an electrode subjected to the voltage measurement results in a different network from the signal source Vs to the electrodes, and different resistance values are determined even at the same electrode. Specifically, in the portions (a)-(c) of FIG. 8, $R_{b1}$ and $R'_{b1}$, each represent a resistance value from the signal source Vs to the electrodes 21, $R_{b2}$, and $R'_{b2}$, each represent a resistance value from the signal source Vs to the electrodes 22, and $R_{b3}$, and $R'_{b3}$ each represent a resistance value from the signal source Vs to the electrodes 23. However, the relations $R_{b1}=R'_{b1}$, $R_{b2}=R'_{b2}$, and $R_{b3}=R'_{b3}$ do not hold. Here, if the assumption is made that values $\Delta R_{b1}=R_{b1}-R'_{b1}$, $\Delta R_{b2}=R_{b2}-R'_{b2}$, $\Delta R_{b3}=R_{b3}-R'_{b3}$ are sufficiently small, the position of the signal source Vs may be detected, regarding that the relations $R_{b1}=R'_{b1}$, $R_{b2}=R'_{b2}$, and $R_{b3}=R'_{b3}$ hold.

In this embodiment, a ratio (attenuation ratio) $V'_{12}/V_{12}$ between the first voltage $V_{12}$ and the second voltage $V'_{12}$ that are generated between the electrode 21 (ground potential) and the electrode 22 (i.e., between the channels $ch_1$ and $ch_2$) is given by eq. (21). Here, the first voltage $V_{12}$ and the second voltage $V'_{12}$ are generated between the electrodes 21 and 22 respectively when no external resistance is connected between the electrodes 21 and 22 and when external resistance Rg is connected between the electrodes 21 and 22.

[Eq. 21]

$$\frac{V'_{12}}{V_{12}} = \frac{R_g}{R_{b1} + R_{b2} + R_g} \quad \text{(Eq. 21)}$$

Here, $R_{b1}$ represents a value of internal resistance between the signal source Vs in the living body 10 and the electrode 21 ($ch_1$), and $R_{b2}$ represents a value of internal resistance between the signal source Vs and the electrode 22 ($ch_2$). It is regarded that the relation $R'_{b1}=R_{b1}$ holds.

Likewise, a ratio (attenuation ratio) $V'_{23}/V_{23}$ between the first voltage $V_{23}$ and the second voltage $V'_{23}$ that are generated between the electrode 22 (ground potential) and the electrode 23 (i.e., between the channels $ch_2$ and $ch_3$) is given by eq. (22). A ratio (attenuation ratio) $V'_{31}/V_{31}$ between the first voltage $V_{31}$ and the second voltage $V'_{31}$ that are generated between the electrode 23 (ground potential) and the electrode 21 (i.e., between the channels $ch_3$ and $ch_1$) is given by eq. (23).

[Eq. 22]

$$\frac{V'_{23}}{V_{23}} = \frac{R_g}{R_{b2} + R_{b3} + R_g} \quad \text{(Eq. 22)}$$

[Eq. 23]

$$\frac{V'_{31}}{V_{31}} = \frac{R_g}{R_{b3} + R_{b1} + R_g} \quad \text{(Eq. 23)}$$

Here, $R_{b3}$ represents a value of internal resistance between the signal source Vs in the living body 10 and the electrode 23 ($ch_3$). It is regarded that the relations $R'_{b2}=R_{b2}$ and $R'_{b3}=R_{b3}$ hold.

Consequently, the eqs. (21), (22), and (23) are the same as the eqs. (12), (13), and (14) described in the second embodiment. Thus, like second embodiment, the sums of the distances ($D_1+D_2$), ($D_2+D_3$), and ($D_3+D_1$) between the electrodes 21, 22, and 23 and the signal source Vs are expressed by the above-described eqs. (15), (16), and (17). Therefore, the three-dimensional position coordinates (x, y, z) of the signal source Vs may be determined by solving the eqs. (18), (19), and (20) of the three ellipses $E_1$, $E_2$, and $E_3$ above described. Here, the ellipse $E_1$ has the focal points at the electrodes 21 and 22 (the channels $ch_1$ and $ch_2$), the ellipse $E_2$ has the focal points at the electrodes 22 and 23 (the channels $ch_2$ and $ch_3$), and the ellipse $E_3$ has the focal points at the electrodes 23 and 21 (the channels $ch_3$ and $ch_1$).

According to this embodiment, the ground electrode does not have to be arranged on the surface of the living body 10. Thus, this embodiment has a simpler configuration and enables accurate detection of the three-dimensional position of the signal source Vs in the living body.

The present invention has been described with reference to the beneficial embodiments. The above description is not intended to limit the present invention, and various modifications may naturally be made to the present invention. For example, although the position of the signal source Vs is detected in the embodiments described above, the potential and position of the signal source Vs may naturally be detected at the same time.

In the first embodiment described above, the three-dimensional position coordinates (x, y, z) of the signal source Vs are determined by solving the eqs. (9), (10), and (11) of the three spheres $Q_1$, $Q_2$, and $Q_3$. However, if the value $R_{b0}$ of internal resistance between the signal source Vs and the ground electrode 20 is defined as an unknown, the three-dimensional position coordinates (x, y, z) of the signal source Vs are determined by solving the eqs. (18), (19), and (20) of the three ellipses $E_1$, $E_2$, and $E_3$ described in the second embodiment. In this case, the ellipse $E_1$ has the focal points at the electrode 21 (the channel $ch_1$) and the ground electrode 20, the ellipse $E_2$ has the focal points at the electrode 22 (the channel $ch_2$) and the ground electrode 20, and ellipse $E_3$ has the focal points at the electrode 23 (the channel $ch_1$) and the ground electrode 20.

In the second embodiment described above, the three-dimensional position coordinates (x, y, z) of the signal source Vs are determined by solving the eqs. (18), (19), and (20) of the three ellipses $E_1$, $E_2$, and $E_3$. However, the eqs. (18), (19), and (20) may be changed to equations respectively expressing the three unknowns $R_{b1}$, $R_{b2}$, and $R_{b3}$, and the three-dimensional position coordinates may be determined by solving the equations of the three spheres.

In the embodiments described above, the three electrodes 21, 22, and 23 are arranged on the surface of the living body 10. However, to detect the position of the signal source Vs with higher accuracy, more than three electrodes may be arranged. Further, although one ground electrode was arranged in the embodiments described above, two or more ground electrodes may be arranged.

In the embodiments described above, the first external resistance and the second external resistance are connected in parallel between the electrodes 21, 22, and 23 and the ground electrode 20, and the switching means SW alternately switches the first and second external resistances. However, the switching means SW does not necessarily has to be used.

Specifically, the electrodes 21, 22, and 23 are comprised of adjacent electrodes 21a and 21b, adjacent electrodes 22a and 22b, and adjacent electrodes 23a and 23b, respectively. A first external resistance Rg1 may be connected to one of the adjacent electrodes of each electrode, namely the electrodes 21a, 22a, or 23a to form a circuit. A second external resistance Rg2 may be connected to the other one of the adjacent electrodes of each electrode, namely the electrodes 21b, 22b, or 23b to form another circuit. In this manner, first and second voltages generated at each of the electrodes 21, 22, and 23 may be measured, thereby detecting the position of the signal source Vs in the living body.

Figure 9:
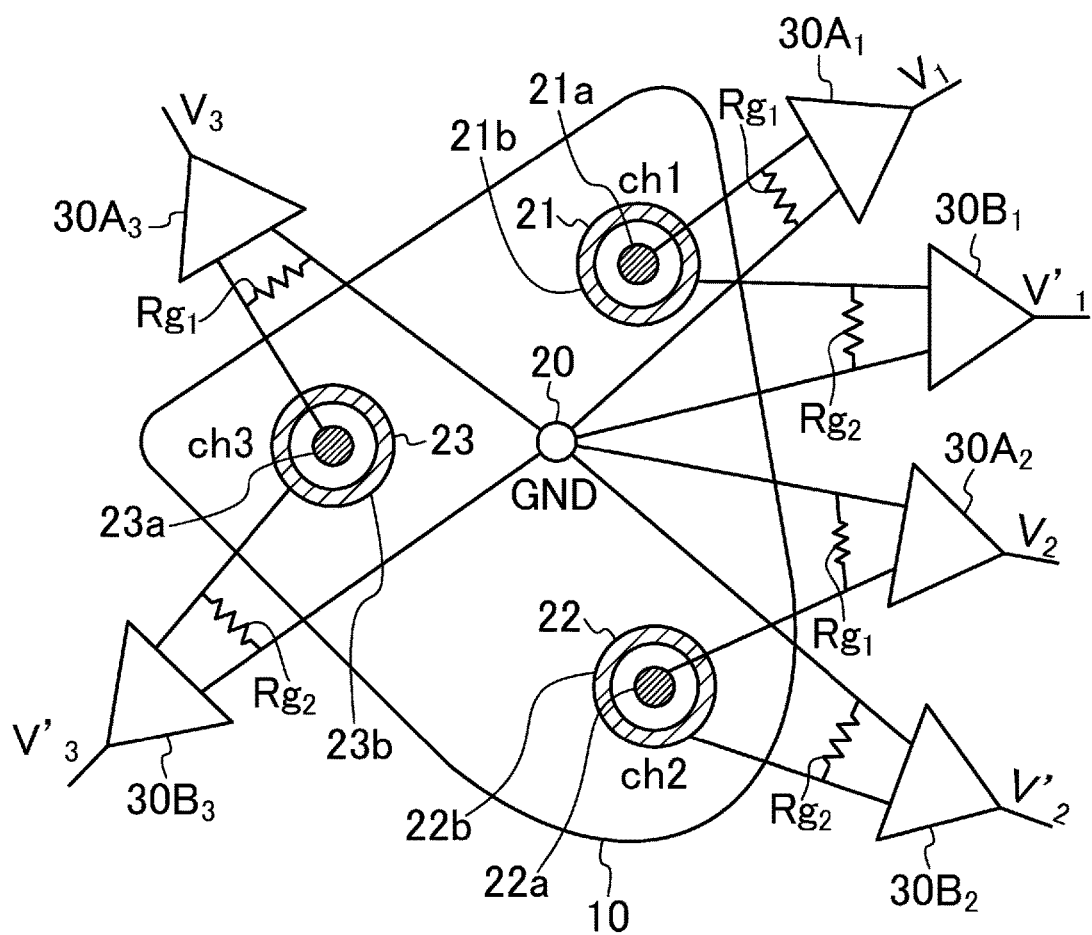
FIG. 9 is a network diagram describing a method for detecting a position of a signal source in a living body, according to another embodiment of the present invention.

Here, FIG. 9 illustrates an exemplary network in which the switching means SW is not used. Note that a signal source Vs, internal resistances $R_{b1}$, $R_{b2}$, $R_{b3}$, and $R_{b0}$ between the signal source Vs and the electrode 21 (21a, 21b), the electrode 22 (22a, 22b), the electrode 23 (23a, 23b), and the ground electrode 20 are omitted from FIG. 9. In the network of FIG. 9, the first external resistance Rg1 and the second external resistance Rg2 are each connected in parallel between the three electrodes 21 (21a, 21b), 22 (22a, 22b), 23 (23a, 23b) and the ground electrode 20 that are arranged on a surface of the living body 10. A first voltage $V_1$ which is generated when the first external resistance Rg1 is connected in parallel between the electrode 21a and the ground electrode 20 is amplified and measured by an amplifier $30A_1$. A second voltage $V'_1$ generated when the second external resistance Rg2 is connected in parallel between the electrode 21b and the ground electrode 20 is amplified and measured by an amplifier $30B_1$. Likewise, a first voltage $V_2$ which is generated when the first external resistance Rg1 is connected in parallel between the electrode 22a and the ground electrode 20 is amplified and measured by an amplifier $30A_2$. A second voltage $V'_2$ which is generated when the second external resistance Rg2 is connected in parallel between the electrode $22_b$ and the ground electrode 20 is amplified and measured by an amplifier $30B_2$. A first voltage $V_3$ which is generated when the first external resistance Rg1 is connected in parallel between the electrode 23a and the ground electrode 20 is amplified and measured by an amplifier $30A_3$. A second voltage $V'_3$ which is generated when the second external resistance Rg2 is connected in parallel between the electrode 23b and the ground electrode 20 is amplified and measured by an amplifier $30B_3$. In this case, it is conceivable to use, for example, wires to connect the first external resistance Rg1 and the second external resistance Rg2 in parallel between each of the electrodes 21 (21a, 21b), 22 (22a, 22b), and 23 (23a, 23b) and the ground electrode 20.

DESCRIPTION OF REFERENCE CHARACTERS

10 Living Body
20 Ground Electrode
21 First Electrode (Channel $ch_1$)
22 Second Electrode (Channel $ch_2$)
23 Third Electrode (Channel $ch_3$)
30 Amplifier (Measurer)

The invention claimed is:

1. A method for detecting a position of a signal source in a living body, based on voltages generated at a set of electrodes arranged on a surface of the living body, the method comprising:
arranging the set of electrodes including at least three electrodes on the surface of the living body and alternately connecting a first external resistance and a second external resistance in parallel between the set of electrodes and a ground potential;
measuring the voltages including first voltages $V_i$ (i=1, 2, 3) which are generated at the respective electrodes when the first external resistance is connected in parallel between the set of electrodes and the ground potential, and second voltages $V'_i$ (i=1, 2, 3) which are generated at the respective electrodes when the second external resistance is connected in parallel between the set of electrodes and the ground potential; and calculating three ratios $V_i/V'_i$ (i=1, 2, 3) from the first voltages $V_i$ and the second voltages $V'_i$, and detecting the position of the signal source in the living body based on the three ratios $V_i/V'_i$ (i=1, 2, 3).

2. The method of claim 1, wherein
a ground electrode is arranged on the surface of the living body, and
the first and second external resistances are alternately connected in parallel between the set of electrodes and the ground electrode.

3. The method of claim 1, wherein
when the first and second voltages $V_i$ and $V'_i$ generated at one of the electrodes are measured, at least one of the other two electrodes is connected to the ground potential.

4. A method for detecting a position of a signal source in a living body, based on voltages generated at electrodes arranged on a surface of the living body, the method comprising:
arranging the electrodes including a first electrode, a second electrode, and a third electrode on the surface of the living body;
alternately connecting a first external resistance and a second external resistance in parallel between the first and second electrodes, between the second and third electrodes, and the third and first electrodes;
measuring first voltages $V_{12}$, $V_{23}$, and $V_{31}$ which are generated between the respective electrodes when the first external resistance is connected in parallel between the respective electrodes, and second voltages $V'_{12}$, $V'_{23}$, and $V'_{31}$ which are generated between the respective electrodes when the second external resistance is connected in parallel between the respective electrodes; and
calculating three ratios $V_{12}/V'_{12}$, $V_{21}/V'_{21}$, and $V_{31}/V'_{31}$ respectively from the first voltages $V_{12}$, $V_{23}$, $V_{31}$ and the second voltages $V'_{12}$, $V'_{23}$, and $V'_{31}$, and detecting the position of the signal source in the living body based on the three ratios $V_{12}/V'_{12}$, $V_{21}/V'_{21}$, and $V_{31}/V'_{31}$.

5. The method of claim 1, wherein
one of the first external resistance or the second external resistance has an infinite resistance value.

6. The method of claim 1, wherein
measurements of the first and second voltages are repeated as one cycle to acquire time-series measurement data of the voltage ratios through repetition of the cycle, and
a trajectory of movement of the position of the signal source in the living body is detected based on the acquired time-series measurement data.

7. A device for detecting a position of a signal source in a living body, based on voltages generated at a set of electrodes arranged on a surface of the living body, the device comprising:
at least three electrodes forming the set of electrodes and being arrangeable on the surface of the living body;
a connector alternately connecting a first external resistance and a second external resistance in parallel between the set of electrodes and a ground potential;
a measurer measuring, in a state where the set of electrodes has been arranged on the surface of the living body, first voltages $V_i$ (i=1, 2, 3) which are generated at the respective electrodes when the connector connects the first external resistance in parallel between the set of electrodes and the ground potential, and second voltages $V'_i$ (i=1, 2, 3) which are generated at the respective electrodes when the connector connects the second external resistance in parallel between the set of electrodes and the ground potential; and
a detector calculating three ratios $V_i/V'_i$ (i=1, 2, 3) from the first voltages $V_i$ and the second voltages and detecting the position of the signal source in the living body based on the three ratios $V_i/V'_i$ (i=1, 2, 3).

8. A device for detecting a position of a signal source in a living body, based on voltages generated at electrodes arranged on a surface of the living body, the device comprising:
the electrodes including a first electrode, a second electrode, and a third electrode which are arrangeable on the surface of the living body;
a connector alternately connecting a first external resistance and a second external resistance in parallel between the first and second electrodes, between the second and third electrodes, and the between third and first electrodes;
a measurer measuring, in a state where the electrodes have been arranged on the surface of the living body, first voltages $V_{12}$, $V_{23}$, and $V_{31}$ which are generated between the respective electrodes when the connector connects the first external resistance in parallel between the respective electrodes, and second voltages $V'_{12}$, $V'_{23}$, and $V'_{31}$ which are generated between the respective electrodes when the connectors connects the second external resistance in parallel between the respective electrodes; and
a detector calculating three ratios $V_{12}/V'_{12}$, $V_{21}/V'_{21}$, and $V_{31}/V'_{31}$ respectively from the first voltages $V_{12}$, $V_{23}$, $V_{31}$ and the second voltages $V'_{12}$, $V'_{23}$, and $V'_{31}$, and detecting the position of the signal source in the living body based on the three ratios $V_{12}/V'_{12}$, $V_{21}/V'_{21}$, and $V_{31}/V'_{31}$.

* * * * *